US00PP36750P2

(12) United States Plant Patent
Grazzini

(10) Patent No.: US PP36,750 P2
(45) Date of Patent: Jun. 17, 2025

(54) ***HIBISCUS* PLANT NAMED 'G21087'**

(50) Latin Name: *Hibiscus moscheutos*
Varietal Denomination: G21087

(71) Applicant: Garden Genetics llc, Columbus, OH (US)

(72) Inventor: Richard A. Grazzini, Columbus, OH (US)

(73) Assignee: Garden Genetics, Columbus, OH (US)

( * ) Notice: Subject to any disclaimer, the term of this patent is extended or adjusted under 35 U.S.C. 154(b) by 0 days.

(21) Appl. No.: 18/933,419

(22) Filed: Oct. 31, 2024

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Hibiscus moscheutos* plant named 'G21087' is disclosed, characterized by large light pink flowers with distinct dark veins radiating from the central eye out into the petals. Flower size is large, about 7 to 8 inches. Young foliage is deep purple, and a deep purple flush is maintained on mature foliage. Plants are compact, growing to approximately 36 to 42 inches high and wide with dense basal branching. Plants emerge and flower earlier than is typical of the species. Plants have been shown Winter hardy to USDA Zone 5. The new variety is a *Hibiscus moscheutos*, normally produced as an outdoor garden or container plant.

2 Drawing Sheets

Figure 1:
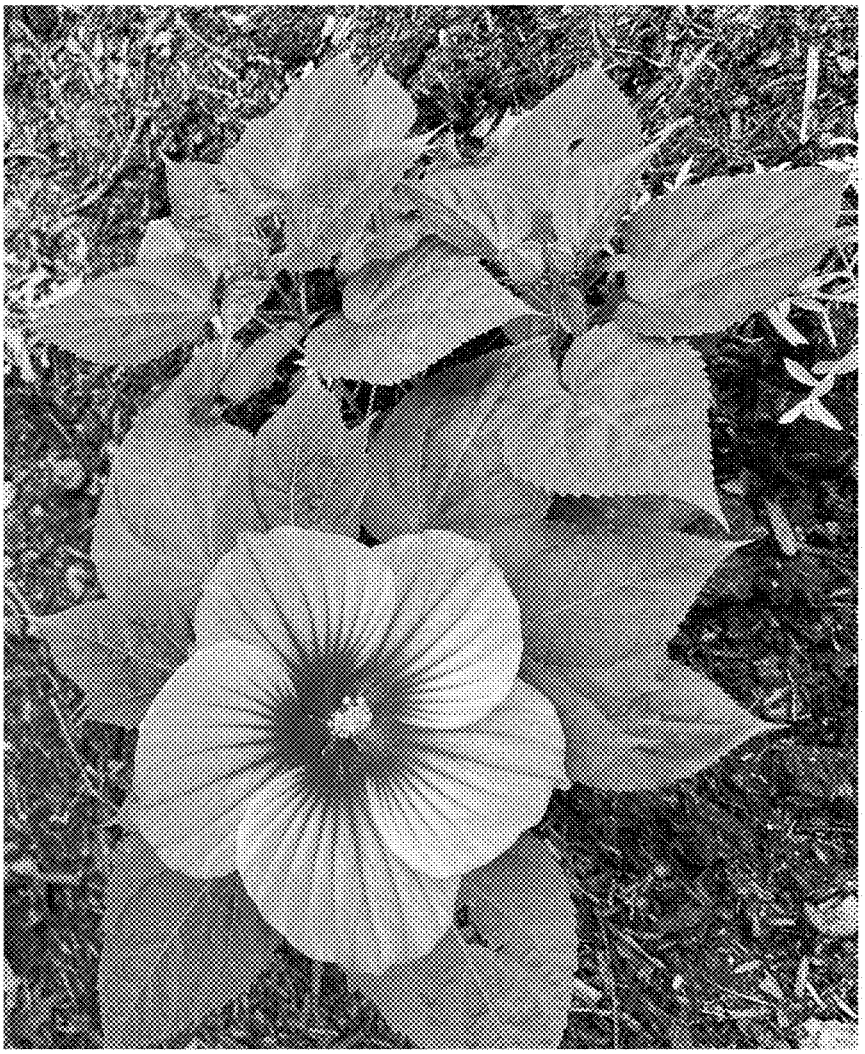

Latin name of the genus and species: *Hibiscus moscheutos*.

Cultivar denomination: 'G21087'.

BACKGROUND OF THE INVENTION

The new cultivar is the product of a planned breeding program conducted by the inventor. The self-pollination resulting in the new cultivar was made between June 2016 and September 2017 at a research greenhouse in Bellefonte, Pennsylvania. The parent cultivar is an undistributed, unpatented proprietary cultivar referred to internally as '43450-4'. The new cultivar 'G21087' was derived from self-pollinating '43450-4'. Selection of 'G21087' was made at the same research greenhouse in Bellefonte, PA in August of 2019.

Asexual reproduction of the new cultivar 'G21087' by terminal vegetative cuttings was performed at the same nursery in Bellefonte, Pennsylvania in June of 2020. Subsequent asexual reproduction, including from tissue culture has shown that the unique features of this cultivar are stable and reproduced true to type through successive generations.

SUMMARY OF THE INVENTION

The cultivar 'G21087' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G21087'. These characteristics in combination distinguish 'G21087' as a new and distinct *Hibiscus* cultivar:

1. 'G21087' has large (6-8" in diameter) light pink flowers, with a large red eye, and with distinct dark veins radiating from the central eye out into the petals, with the central-most 3 to 5 dark veins on each petal reaching or almost reaching the outer petal edge.
2. The leaves of 'G21087' are chocolate-brown to dark violet, with a slightly pubescent, non-glossy leaf surface, upper and lower surfaces.
3. 'G21087' produces more shoots than typical when it emerges from dormancy in the spring. Shoot count at emergence of new cultivar 'G21087' is 5 to 8 shoots or more.
4. Emergence from dormancy of 'G21087' occurs about 4 weeks earlier than typical for a *Hibiscus moscheutos* cultivar.
5. 'G21087' begins to flower 3 to 4 weeks earlier than typical for the species.
6. 'G21087' is compact and densely branched, forming a mound about 36" to 40" in height and width.
7. New cultivar 'G21087' has been shown to be winter hardy in USDA zone 5.

PARENT COMPARISON

Plants of the new cultivar 'G21087' are similar to plants of the parent cultivar, in most horticultural characteristics. However, plants of the new cultivar 'G21087' differ in the following:

1. The new cultivar 'G21087' has light pink flowers, with a large red eye, and with distinct dark veins radiating from the central eye out into the petals, with the central-most 3 to 5 dark red veins on each petal reaching or almost reaching the outer petal edge. In contrast, parent '43450-4' has dark pink flowers, a dark red-violet eye, and darker petal veins.

2. The leaves of 'G21087' are chocolate-brown to dark violet, with a slightly pubescent, non-glossy leaf surface, above and below. '43450-4' has much more pubescent bronze to chocolate-brown leaves, with a dull, matte leaf surface.
3. 'G21087' produces more shoots than '43450-4' when it emerges from dormancy in the Spring. Shoot count at emergence of new cultivar 'G21087' is 5 to 8 shoots or more, whereas '43450-4' has 2 to 4 shoots at emergence.
4. Emergence from dormancy of 'G21087' occurs about 4 weeks earlier than does that of '43450-4'.
5. 'G21087' begins to flower 3 to 4 weeks earlier than parent '43450-4'.

COMMERCIAL COMPARISON

'G21087' can be compared to the commercially known cultivar *Hibiscus* 'Cherry Cheesecake', U.S. Plant Pat. No. 26,089. These plants are similar in most horticultural characteristics. However, plants of the new cultivar 'G21087' differ in the following:

1. 'G21087' has large (6-8" in diameter) light pink flowers, with a large red eye, and with distinct dark veins radiating from the central eye out into the petals, with the central-most 3 to 5 dark veins on each petal reaching or almost reaching the outer petal edge. This comparator has white flowers with magenta-tipped petals and magenta veining radiating out from a cherry-red eye. Petal venation of the comparison cultivar is much less extensive than in new cultivar 'G21087'.
2. The leaves of 'G21087' are chocolate-brown to dark violet, with a slightly fuzzy, non-glossy leaf surfaces, above and below. This comparator cultivar has green leaves, with some bronze shading, and a dull matte leaf surface.
3. This comparison cultivar is 3 to 4 weeks later to emerge from dormancy than the new cultivar 'G21087'.
4. 'G21087' begins to flower 3 to 4 weeks earlier than this comparator.
5. 'G21087' is compact and densely branched, forming a mound about 36" to 40" in height and width, whereas this comparator forms an upright oval shape reaching 56" to 72" in height and 48" to 60" in width.

'G21087' can also be compared to the commercially known cultivar *Hibiscus* 'PAS351671', unpatented. These cultivars are similar in most horticultural characteristics. However, plants of the new cultivar 'G21087' differ in the following ways:

1. 'G21087' has light pink flowers with a red eye, and distinct dark red venation radiating from the central red eye. This comparator has white flowers, a red eye, and no venation.
2. 'G21087' has chocolate-brown to dark violet leaves, whereas this comparator has medium green foliage.
3. 'G21087' emerges 2 to 3 weeks earlier than this comparator when overwintered in-ground or in-container.
4. 'G21087' flowers up to two weeks earlier than this comparator when overwintered in-ground or in-container.
5. 'G21087' has a compact plant habit, 36" to 42" high and wide, and with dense basal branching. This comparator is more compact, about 24" to 30" high and wide.

BRIEF DESCRIPTION OF THE PHOTOGRAPHS

The accompanying photograph in FIG. 1 illustrates a 16-month old flowering plant in Summer (August).

Figure 2:
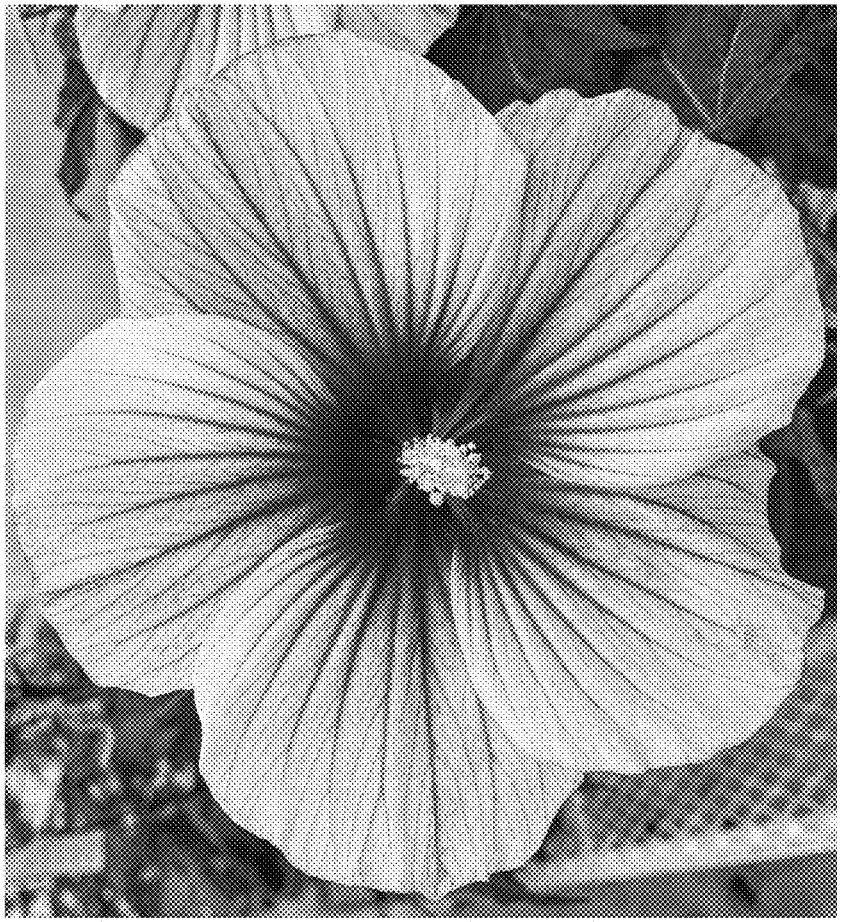

FIG. 2. is a close-up view of a typical flower of 'G21087'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart 2015, except where general terms of ordinary dictionary significance are used. The following observations and measurements describe 'G21087' plants grown outdoors from Spring to early Summer in Camarillo, California. The growing temperature ranged from about 7° C. to 30° C. during the day and from about 5° C. to 12° C. during the night. General light conditions are bright, normal sunlight. Measurements and numerical values represent averages of typical plant types. Plants are approximately 4 months old from a large rooted cutting. No chemical or photoperiodic treatments were given.

Botanical classification: *Hibiscus moscheutos* 'G21087'.

PROPAGATION

Root description: Woody, moderately well branched. Colored near Brown N200C, N200D and Grey 201B.

PLANT

Growth habit: Upright and somewhat outward. Moderately dense branching and foliage.
Height: Approximately 90 cm to 105 cm.
Plant spread: Approximately 90 cm to 105 cm.
Growth rate: Moderate.
Branching characteristics: Basal and lateral branching.
Length of branches: Approximately 35 to 70 cm.
Diameter branches: Approximately 7 to 10 mm.
Quantity of branches: Approximately 5 to 8 main basal branches.
Texture of lateral branches: Glabrous. Slightly glaucous.
Color of lateral branches:
*Young*.—Near RHS Greyed-Purple N186C with thin glaucous layer N187C. Nodes flushed Red-Purple N66B.
*Mature*.—Near RHS Green 137C, moderate flushing N186C and N186D.
Aspect: Approximately 30° to 60° angle from center of plant.
Strength of lateral branches: Very strong.
Internode length: Average range 3 to 7 cm.

FOLIAGE

*Arrangement*.—Alternate.
*Average length*.—Average range 6 to 10 cm.
*Average width*.—Average range 4 to 6.3 cm.
*Shape of blade*.—Ovate.

*Apex*.—Acuminate.
*Base*.—Rounded.
*Attachment*.—Petiolate.
*Margin*.—Moderately serrate.
*Texture of top surface*.—Sparsely pubescent.
*Texture of bottom surface*.—Sparsely pubescent with protruding mid-vein.
*Foliage color*.—Young foliage upper side: Near RHS Greyed-Purple N186A., center vein. Young foliage under side: Near RHS Greyed-Purple 186A flushed 185A. Mature foliage upper side: Near RHS Green 139A flushed N186A. Mature foliage under side: Near RHS Green 137C. Slightly flushed 185A.
*Venation*.—Type: Pinnate. Venation color upper side: Young foliage: Near RHS Red-Purple 58B. Mature foliage: Near Red-Purple 59D, fading distally to Greyed-Red 181D. Venation color under side: Young foliage: Near RHS Greyed-Purple 186B. Mature foliage: Near Greyed-Orange 168D.

Petiole:
*Length*.—Average range 4 to 8 cm.
*Diameter*.—Average 4 mm.
*Color*.—Near RHS Red-Purple 58C flushed 58C.
*Texture*.—Finely pubescent.

INFLORESCENCE

Flower type and habit: Single, rotate, overlapping.
Flower longevity on plant: 2 to 3 days.
Persistence: Self-cleaning.
Fragrance: None.

Bud:
*Shape*.—Ovate.
*Length*.—3.9 cm.
*Diameter*.—2.5 cm at widest.
*Shape*.—Ovate.
*Texture*.—Scabrid.
*Color*.—RHS Green 143C.

Flower size:
*Diameter*.—15 to 20 cm.
*Depth*.—8 cm.

Petals:
*Quantity*.—5.
*Arrangement*.—Rotate. Moderately overlapping.
*Length*.—7 to 11 cm.
*Width*.—6.5 to 8 cm at widest.
*Shape*.—Orbicular to obovate.
*Apex*.—Rounded with very shallow and irregular crenations.
*Base*.—Broad taper.
*Margin*.—Entire.
*Texture, upper and lower surfaces*.—Glabrous, slightly iridescent to shiny.
*Color*.—Eye-size and feathering: Eye extends about 20% to 30% length of petal from petal base. Distinct dark vein color is neat along the veins, with little feathering. This dark vein coloration extends almost to margins with the mid veins. Extension of smaller veins is about 50 to 60% of petal length. When opening, upper surface: Near RHS Red-Purple 63D. Distinct vein coloration near N57A. When opening, upper surface, eye color: RHS Red-Purple N57A. When opening, lower surface: Near RHS Red-Purple 65C. Flush along veins N66C. Fully opened, upper surface: Near RHS Red-Purple 63D. Distinct vein coloration near N66B. Fully opened, upper surface, eye color: RHS Red-Purple N66B. Fully opened, lower surface: Near RHS Red-Purple 65D. Flush along veins N66C.

Calyx sepals:
*Quantity*.—5.
*Length*.—3.5 cm.
*Width*.—1.7 cm at widest part.
*Shape* (*overall*).—Deltate. Apex: Acute. Base: Truncate, fused.
*Margin*.—Entire.
*Color*.—Near RHS Yellow-Green 144C.
*Texture*.—Lightly pubescent.

Epicalyx sepals:
*Quantity*.—5 to 7, typically 6.
*Length*.—2.1 cm.
*Width*.—5 mm at widest part.
*Shape* (*overall*).—Linear-lanceolate, fused at base; campanulate overall.
*Apex*.—Acute.
*Base*.—Truncate.
*Margin*.—Entire.
*Color*.—RHS Yellow-Green 145B flushed 145A.
*Texture*.—Lightly pubescent.

Peduncle:
*Length*.—Average range 4 to 6 cm.
*Diameter*.—5 mm.
*Angle*.—45° to the lateral branch.
*Strength*.—Moderately strong.
*Texture*.—Slightly pubescent.
*Color*.—RHS Yellow-Green 145A.

REPRODUCTIVE ORGANS

Stamen stalk:
*Length*.—6.8 cm.
*Diameter*.—6 mm at base, tapering to 4 mm near apex.
*Color*.—Red-Purple 65A.
*Protruding beyond petals*.—Non-protruding.

Stamens:
*Quantity*.—Typically between 40 and 50.

Anthers:
*Shape*.—Globular.
*Length*.—Approximately 2 mm.
*Color*.—RHS Yellow-White 158D.
*Pollen*.—Color: RHS Yellow-White 158D. Quantity: Sparse.

Pistil:
*Number*.—5.
*Length*.—8 mm.
*Style*.—Length: 5 mm. Color: Near RHS Red-Purple 69D.
*Stigma*.—Shape: Oblately globular. Color: RHS Red-Purple 69A. Ovary Color: RHS Green-White 157A.

OTHER CHARACTERISTICS

Disease resistance: Neither resistance nor susceptibility to diseases or pests normal to *Hibiscus* have been observed in this cultivar.
Drought tolerance and temperature tolerance: Hardy perennial, USDA zones 5-9.
Fruit/seed production: Not observed to date.

What is claimed is:

1. A new and distinct cultivar of *Hibiscus moscheutos* plant named 'G21087' as illustrated and described herein.

* * * * *